Figure 1A:
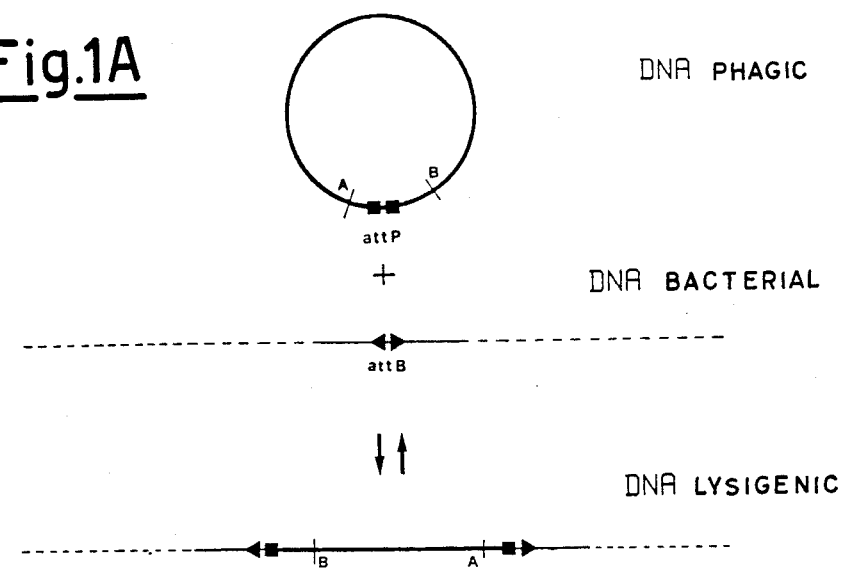

United States Patent [19]

Rappuoli

[11] Patent Number: 4,925,792
[45] Date of Patent: May 15, 1990

[54] PROCESS FOR PRODUCING PROTEINS CORRELATED WITH THE DIPHTHERIC TOXIN

[75] Inventor: Rino Rappuoli, Quercegrossa Monteriggioni, Italy

[73] Assignee: Sclavo, S.p.A., Siena, Italy

[21] Appl. No.: 575,335

[22] Filed: Jan. 31, 1984

[30] Foreign Application Priority Data

Feb. 8, 1983 [IT] Italy ............................ 19462 A/83
Dec. 5, 1983 [IT] Italy ............................ 24020 A/83

[51] Int. Cl.$^5$ ................. C12P 21/00; C12N 15/00; C12N 7/00; C12R 1/16
[52] U.S. Cl. ......................... 435/69.1; 435/69.3; 435/172.3; 435/252.3; 435/320; 435/844; 935/31; 935/38; 935/58; 935/61; 935/12; 935/29; 935/72
[58] Field of Search ............ 435/68, 235, 172.3, 435/70, 252.3, 320, 844; 935/12, 29, 38, 56, 72, 31

[56] References Cited

PUBLICATIONS

Rappuoli et al. (Jan. 18, 1983), *J. Virology*, vol. 45, pp. 524–530.
Uchida et al. (1973), *J. Biological Chemistry*, vol. 248, pp. 3838–3844.
Groman et al. (1979), *Infection and Immunity*, vol. 26, pp. 1065–1070.
Uchida, T. et al., 1973, JBC, 248: 3838.
Rappuoli, R. et al., Feb. 1983, J. Virol, 45: 524.
Ishii-Kanei, C. et al., Sep. 1979, Infection and Immunity, 25: 1081.
Groman, N. and K. Judge, Dec. 1979, Infection and Immunity, 26: 1065.
Rappuoli, R. et al., Feb. 1985, Bio/Technology, p. 161.
Uchida et al. (1973), J. Biol. Chem., 248: 3838–3844.
Rappuoli et al. (1983), J. Bact., 153: 1202–1210.
Rappuoli (1983), Appl. Env. Microbiol., 46: 560–564.

*Primary Examiner*—Thomas G. Wiseman
*Attorney, Agent, or Firm*—Hedman, Gibson, Costigan & Hoare

[57] ABSTRACT

Process for the production of a protein correlated with the diphtheric toxin which comprises culturing in a liquid nutrient medium having a concentration of iron ions of from 0.05 μg/ml to 0.5 μg/ml, at a temperature of from 30° C. to 40° C., in a neutral culturing environment and under aerobic conditions, a microorganism belonging to the *Corynebacterium diphtheriae* genus with two mutant phages encoding the protein correlated with the diphtheric toxin integrated in a nontandem mode in their chromosomes.

3 Claims, 3 Drawing Sheets

PROCESS FOR PRODUCING PROTEINS CORRELATED WITH THE DIPHTHERIC TOXIN

This invention relates to a process for the production of a protein which is correlated with the diphtheric toxin, by culturing in a liquid nutrient medium having a concentration of iron ions of from 0.05 $\mu$g/ml to 0.5 $\mu$g/ml at a temperature of from 30° C. to 40° C., in a neutral culturing environment and under aerobic conditions, a microorganism belonging to the *Corynebacterium diphtheriae* genus with two mutant phages encoding the protein correlated with the diphtheric toxin in a nontandem mode in their chromosomes.

The diphtheric toxin is a protein which is outstandingly toxic towards the eukaryotic cells.

Such toxin consists of two sub-units, viz.: the B-fragment which is capable of becoming bonded to the receptors which are present on the membrane of the eukaryotic cell, and the A-fragment, which is toxic and after having penetrated the cells, blocks the protein synthesis thereof.

The diphtheric toxin is encoded by a gene, whose primary structure has been determined recently (C. Ratti, R. Rappuoli, E. G. Giannini, Nucleic Acid Research, 11, 6589, 6595, (1983), and which is present in the DNA of a few correlated bacteriophages ($\beta,\gamma,\omega$) capable of infecting the *Corynebacterium diphtheriae* (J. J. Costa et al., J. Bacteriol., 148, 124–130 (1981); V. Freeman, J. Bacteriol. 61, 675–688 (1951)).

These phages, after having infected the bacterium, can dissolve same and thus kill it, or can they become integrated in the bacterial chromosome, remain dormant and be replicated whenever the bacterium is replicated.

The DNA of the integrated phage will be transmitted together with the bacterial chromosome to the daughter-cells which will thus contain the protein-encoding gene.

At present, the diphtheric toxin is produced by culturing the $PW_8$ strain and is employed, after detoxication with formol, for the preparation of the antidiphtheric vaccine.

Recently, mutants of the phage $\beta$ have been obtained, by a treatment with nitrosoguanidine, by Uchida et al. (Nature New Biol., 233, 8–11, (1973)).

Such mutant phages which are integrated in the bacterial chromosome of the *Corynebacterium diphtheriae* microorganism, encoded the synthesis of proteins correlated with the diphtheric toxin, wherefrom they differred as to their structure and/or function on account of the presence of one or more mutations inserted in the structural gene of the toxin.

Proteins of the kind referred to above were dubbed Cross-Reacting Materials (CRM), inasmuch as they brought about an immunological cross-reaction with the diphtheric toxin.

Among the several mutant phages which were isolated, there have been more particularly investigated those which encoded for the proteins CRM 176, CRM 197, CRM 228 and CRM 45. (Uchida et al., J. Biol. Chem., 218, 3838–3844 (1973)).

More particularly, the CRM 45 is a protein consisting of a fragment, A, akin to the structure and function of those of the diphtheric toxin, and a fragment, B, which is devoid of a segment capable of binding the protein to the receptors which are present on the surface of the eukaryotic cells.

The result is that CRM 45, even though it has a fragment A which is fully active in vitro, has no in vivo activity at all, inasmuch as it is incapable of penetrating the cells.

Conversely, the fragment B possesses, unaltered, the hydrophobic structure which is necessary to shift the fragment A into the interior of the cell.

On account of these features, that is, presence, of the active fragment A, presence, in the fragment B, of the structure which is required for shifting the fragment A into the cell interior, and absence of the region which is capable of recognizing the receptors of the cell membranes, it had been envisaged to exploit the CRM 45 for building up hybrid toxins. As a matter of fact, by replacing the lacking segment by a substance such as: antibody, monoclonal antibody, hormone or other substance of biological interest, capable of recognizing specific molecules on the surfaces of a few cells, such as target cells, a hybrid toxin was obtained, which was capable of selectively killing a few kinds of cells only. Such hybrid toxin may find an elective application in the pharmacological field and, above all, in the treatment of a few kinds of tumours (P. Bacha et al., J. Biol. Chem., 258, 1565–1570, (1983)).

The CRM 197 protein has the same molecular weight as the diphtheric toxin and is composed of a fragment B which is identical as to its function and structure to those of the toxin, and of a fragment A, which is nontoxic and differs from the original fragment by one aminoacid. The CRM 197, which is atoxic, is immunologically indistinguishable from the diphtheric toxin and can thus be an alternative to the diphtheric toxoid as employed at present for the production of vaccine;

As a matter of fact, a bland treatment of CRM 197 with formol suffices for obtain satisfactory protective levels of diphtheric antibodies in Guinea-pigs (M. Porro et al., J. Infect Dis., 142, 5 (1980)).

Up to now, however, further developments of products deriving from proteins correlated with the diphtheric toxin and obtained according to the procedure as disclosed by Uchida, have been hampered by the low yields of the culturing syntheses of such proteins.

Consequently, an objective of the present invention is to provide a process for the production of proteins correlated with the diphtheric toxin, which comprises the step of culturing in a liquid nutrient medium having a concentration of iron ions of from 0.05 $\mu$g/ml to 0.5 $\mu$g/ml, at a temperature of from 30° C. to 40° C., in a neutral culturing environment and under aerobic conditions, a microorganism belonging to the *Corynebacterium diphtheriae* genus with two mutant phages which are encoding for the protein correlated with the diphtheric toxin and integrated in a nontandem mode in their chromosomes.

More particularly, the object of the present invention is a process for producing CRM 45 with yields of from 50 Lf/ml to 200 Lf/ml and CRM 197 with yields of from 30 Lf/ml to 60 LF/ml by culturing the C7 ($\beta$45) $M_8$ strain with two $\beta$45 mutant phages integrated in a nontandem mode in their chromosomes, and by culturing the C7 ($\beta$197) $M_1$ strain with $\beta$197 phages integrated in a nontandem mode in their chromosomes.

The present invention is essentially based on the rather surprising discovery that the *Corynebacterium diphtheriae* $C_7$ (ATCC 27010) strain possesses in its own chromosome two attachment sites attB whereat the phagic DNA can be integrated. The lysigenic process of a phage after the Campbell's method (Epitomes Adv.

Genetics, 11, 101-145, (1982)) are reported in FIG. 1A, assumes the cleavage of the circular phagic DMA at a specific point, attP, and the integration at an equally specific point of the bacterical chromosome, attB, which is called the attachment site. Up to now, in all the known configurations, a single attP site and a single attB site have been identified.

Figure 1B:
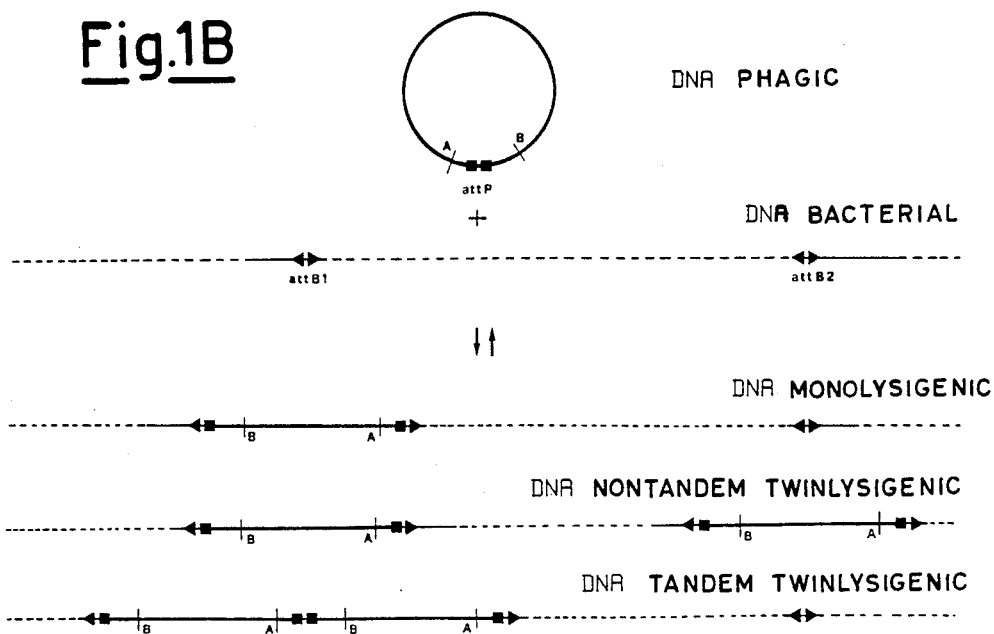

It has now been ascertained that the *Corynebacterium diphtheriae* $C_7$ (ATCC 27010) strain possesses in its chromosome two attachment sites, $attB_1$ and $attB_2$, whereat the phagic DNA can be integrated. By using the TYE culturing medium, as modified by us, there have been isolated, in the lysigenization process of that bacterium, the following lysigenic strains: monolysigens, when the phage is present once only at $attB_1$ or $attB_2$, twinlysigens (tandem) when two phages are simultaneously present at a single attB site, and nontandem twinlysigens, whe two phages are simultaneously present, the one at $attB_1$ and the other at $attB_2$ (FIG. 1B).

According to the present invention, the *Corynebacterium diphtheriae* $C_7$ (ATCC 27010) has been infected with a mutant phage which is encoding for the protein correlated with the diphtheric toxin by plating on a CY culturing medium.

After a 48-hour growth at a temperature of 35° C., lysis plates of the phage have been observed, which contained in their inside an opaque zone due to the growth of those bacteria, in which the phage has been integrated in the bacterial chromosome.

The strains have been drawn in a sterile manner and have been plated on a CY medium so as to isolate the individual colonies, to be analyzed subsequently in order to check the presence of lysigenic phages by the "phage release assay" (Miller et al., Virology, 29, 410-425, (1966)).

A twinlysigen screening has been carried out on the basis of the fact that the lysigens which contained two couples of the integrated phage possessed two encoding genes for the protein correlated to the diphtheric toxin so that they are capable of synthetising a double amount of said protein.

Plates have been prepared, of the TYE culturing medium, each containing 3,4,6,8,12 U/ml of diphtheric antitoxin serum and each lysigen has subsequently been assayed for each individual serum concentration by plate transfer. The protein as produced by the several lysigens by diffusion through the agar-agar, was precipitated from the antibody which was present in the medium, thus forming a halo, the size of which was directly proportional to the quantity of CRM produced by the individual colonies.

In the plates which contained a concentration of antibody of 3 U/ml, all the lysigens formed an identical halo. In those of intermediate concentration, 4-6 U/ml of antibody, there were observed halos of different sizes: very small for the monolysigens and greater for the twinlysigens.

In the plates containing an antibody concentration of from 8 to 12 U/ml, only the twinlysigens exhibited a precipitation halo.

Figure 2:
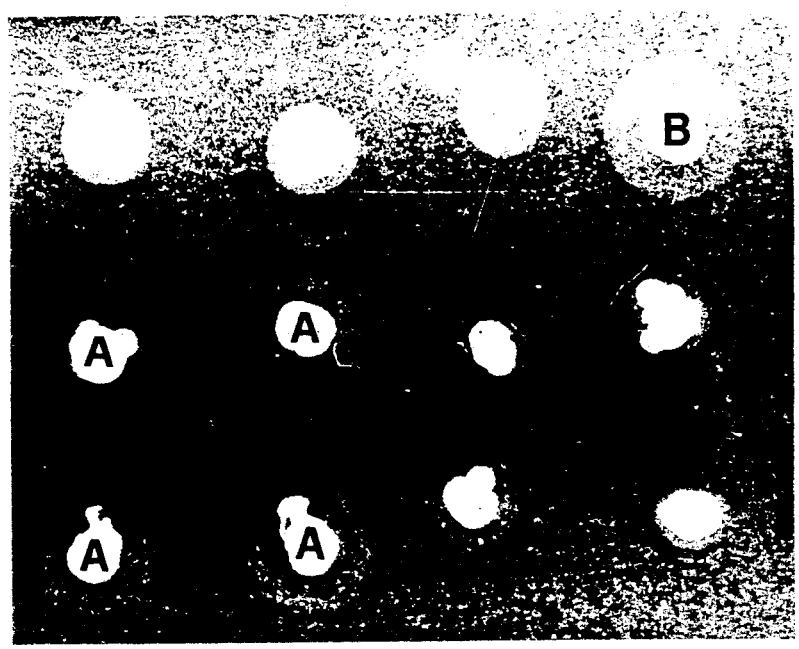

FIG. 2 reports the photograph of a TYE plate containing 6 U/ml of antibody, wherein it is possible to distinguish three halos of different sizes, corresponding to different lysigens: monolysigens (small halo), tandem twinlysigens (halo A) and nontandem twinlysigens (halo B). The demonstration that the lysigens with the greater halo contain two phages integrated in their respective chromosomes has been made by bringing out the molecular organization of the phages by purification of the chromosomal DNA according to conventional procedures.

In FIG. 1R there can be seen that by cleaving the phagic DNA at the points A and B with a restriction enzyme, one obtains an AB fragment, whereas, if the same enzyme is used for the monolysigen, one ought to obtain two fragments, A and B, both containing a portion of the bacterial chromosome, four fragments for the nontandem twinlysigen and three for the tandem twinlysigen. As a matter of fact, the analyses carried out with the procedure of the Southern blot (J. Mol. Biol., 98, 503-517, (1975)), using as the probe the $\beta$Bam 4 fragment containing the attP site labeled with $^{32}P$ reported in FIG. 3, correspond, both by number and position of the bands, to what had been forecast by on the basis of the analysis of FIG. 1B.

Figure 3:
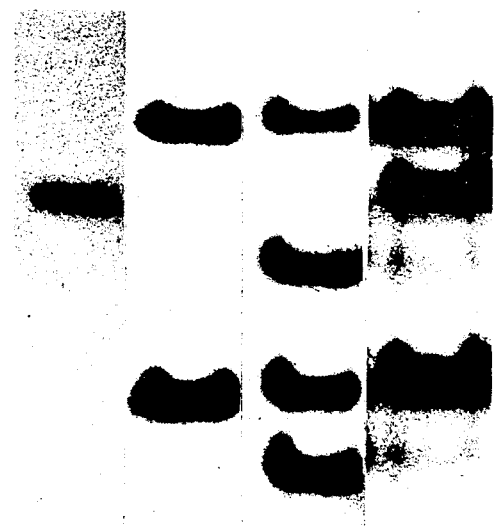
Figure 4:
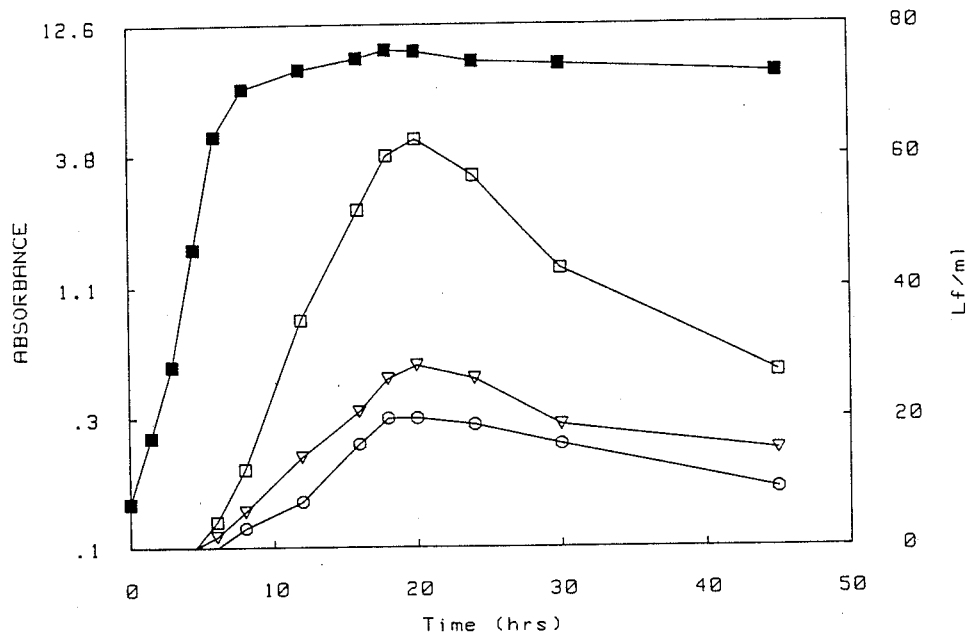

In FIG. 3, the DNA of the phage gives a single band (A), that of the monolysigen two bands (B), that of the nontandem twinlysigen four bands (C), whereas the tandem twinlysigen gives three bands, one of which migrated together with that of the phage (D).

The stability of the twinlysigens has been checked by drawing from old cultures (5-day old) individual colonies, plating them onto CY medium and analyzing with the halo method the presence of the one or two phages. The analysis has been given the following results: the tandem twinlysigens were poorly stable due to their tendency towards missing a phage and being converted into monolysigens. Out of 250 tested colonies, about 180 had become monolysigens, whereas the twinlysigens of the nontandem kind were extremely stable: as a matter of fact, on 450 tested colonies no monolysigen has been found.

According to the present invention, the $C_7$ strain has been infected with the $\beta 45$ mutant phage encoding for the CRM45 protein and the encoding $\beta 197$ phage for the CRM 197 and the following lysigenic strains have been isolated: $C_7$ ($\beta 45$)$M_3$ and $C_7$ ($\beta 197$)$M_5$ (monolysigens), $C_7$ ($\beta 45$) $M_{11}$ and $C_7$ ($\beta 197$)$M_8$ (tandem twinlysigens) and $C_7$ ($\beta 45$)$M_8$ and $C_7$ ($\beta 197$)$M_1$ (nontandem twinlysigens). The strains $C_7$ ($\beta 45$) $M_8$ and $C_7$ ($\beta 197$) $M_1$ have been deposited with the collection center American Type Culture Collection Accession and have been allotted the symbols ATCC-39526 and ATCC-39255.

The several lysigenic strains have been examined for the production of CRM 45 and CRM 197 by growth under aerobic conditions and in a nutrient liquid medium with a concentration of iron ions of from 0.05 $\mu$g/ml to 0.5 $\mu$g/ml, preferably 0.1 $\mu$g/ml, at a temperature of from 30° C. to 40° C., preferably from 35° C. to 37° C. at a pH of neutral value for a period of time as was necessary to build up a considerable quantity of proteins in the culturing medium.

The protein has subsequently been recovered and purified by any of the conventional procedures known to the skilled men.

Culturing media used in the procedure:

TYE medium for producing the precipitation halo.

The following medium has been modified relatively to the original Pappenheimer formula (Inf. Imm., 18, 203-209, (1977)) and has the following composition: Tryptose: 10 g, Yeast Extract: 5 g; NaCl: 5 g; $KH_2PO_4$: 5 g; water: 1 liter.

The pH is ajusted to a value of 7.4 and 2 mls of $CaCl_2$ (50%) are added to the medium prior to autoclaving it.

The precipitate is allowed to settle, whereafter there are added 2 ml/l of a solution II, 1 ml/l of solution III and 12 ml/l of noble agar-agar.

Finally, antidiphtheric horse blood serum is added at a concentrations of 4,6,8 or 12 U/ml consistently with the halo which is expected.

CY medium for the production of CRM proteins.

Yeast Extract: 20 g, casaminoacids 10 g., 1%-tryptophan 5 mls, $KH_2PO_4$ 5 g, water 1 liter, are brought (pH 7.4) to the boil and filtered on Whatman filters when still boiling. There are added 2 mls of solution II, 1 ml of solution III and then the reaction mixture is placed in an autoclave. Prior to using, there are added 3 mls of a solution of maltose and $CaCl_2$ per 100 mls of medium.

Solution II $MgSO_4.7H_2O$ 22.5 g, alanine 115 mg, nicotinic acid 115 mg. There are added then 1 ml of water and conc.HCl to dissolve the components, whereafter there are added 7.5 mg. of pimelic acid, 5 mls of $CuSO_4.5H_2O$ (1%), 4 mls of 1%-$ZnSO_4.5H_2O$, 1.5 mls of 1%-$MnCl_2.4H_2O$ and 3 mls of conc.HCl and water to make up 100 mls.

Solution III

L-cystine 20 g; conc.HCl 20 mls, water to make up 100 mls. Maltose-$CaCl_2$ solution: Maltose 50 g, 2 mls of 50% $CaCl_2$, 1 g of $KH_2PO_4$ and make up to 100 mls with water. The pH is adjusted to 7.4 and the solution is filtered on Whatman 40 paper, whereafter the solution is placed in an autoclave.

DESCRIPTION OF THE DRAWINGS

FIG. 1A: Lysigenization process according to Campbell.

The phagic DNA is broken at a specific point attP and is integrated at an equally specific point, attB, of the bacterial chromosome.

FIG. 1B: lysigenization process in *Corynebacterium diphtheriae* $C_7$ (ATCC 27010). The phagic DNA is broken at the attachment site attP and can be integrated at the two attachment sites $attB_1$ and $attB_2$ which are present in the bacterial chromosome to give: monolysigens, tandem twinlysigens and nontandem twinlysigens.

FIG. 2: Plate with TYE medium containing 6 U/ml of antidiphtheric serum. There can be distinguished 3 precipitation halos, viz.: very small halo (monolysigens), intermediate halo A (tandem twinlysigens) and great halo B (nontandem twinlysigens).

FIG. 3: Analysis of the DNA of the lysigens with the Southern blot method. The DNA has been digested with $BamH_1$ and the fragments have been separated on agarose gel (1.3%) and transferred to nitrocellulose, whereafter they have been hybridized with the $\beta$Bam 4 fragment containing the attP site labeled with $^{32}P$. The $\beta$Bam 4 fragment corresponds to the fragment AB of FIG. 1B. There can be seen a single fragment AB in the phagic DNA (A), two fragments AB in the monolysigen (B), four fragments in the nontandem twinlysigen (C) and three fragments in the tandem twinlysigen (D).

FIG. 4: Production of CRM 197 with the monolysigen strain $C_7$ ($\beta$197)$M_5$: symbol 0; the tandem twinlysigen strain $C_7$ ($\beta$197) $M_8$: symbol ∇; the nontandem twinlysigen strain $C_7$ ($\beta$197)$M_1$: symbol: □.

The solid small squares, ■, indicate the optical density of the culture.

The experimental examples which follow are illustrations and not limitations of the invention.

EXAMPLE 1

125-ml flasks are prepared, containing 10 mls each of CY medium and are sterilized at 120° C. for 15 minutes. The flasks are inoculated with a quantity corresponding to a platinum eyelet of the following lysigenic strains: $C_7$ ($\beta$197) $M_5$, $C_7$ ($\beta$197) $M_8$ and $C_7$ ($\beta$197) $M_1$ which had been grown for 24 hours at 35° C. on CY plates.

The flasks which have been so inoculated are cultured overnight at 35° C.

0.1 ml of each individual culture are inoculated in Erlenmeyer flasks of the capacity of 125 mls. each of which contains 10 mls of deferritized CY medium and supplemented with 0.1 μg/ml of $Fe^{++}$ and placed to incubate on a rotary stirrer at 240 RPM for 45 hrs. at a temperature of 35° C.

Samples are taken at 2-hour intervals, whereon the optical density and the contents of CRM 197 released into the supernatant are determined. The optical density is measured at 590 nm with a Perkin-Elmer Mod. 35 spectrophotometer (light path 1 cm) and CRM 197 is determined with the rocket immunoelectrophoretic method (Murfy et al., J. Clin. Microbiol., 7, 91-96 (1978)) and/or flocculation (G. Ramon, C. R. Soc. Biol., 86, 661-671, (1922)). We intend by Lf/ml the unit of flocculation such as reported by G. Ramon in C. R. Soc. Biol (Paris), 86, 661-671 (1922)).

The results which have been obtained are depicted in FIG. 4. As can be seen, the production of CRM 197 cannot begin before the optical density of the culture has attained a value of 4.5-5 optical densities (O.D.) corresponding to the end of the logarithmic phase. As the end portion of the latter phase is started, the massive production of CRM 197 begins, and continues up to the beginning of the stationary phase (about 20 hours), when the maximum optical density and the maximum amount of CRM 197 are observed.

Beyond the 24th growth hour, a decrease of the CRM 197 production by 25% is observed after 30 hours, and after 45 hours the decrease is 75%. The trend of the production plot of CRM 197 is virtually the same for the different lysigens, whereas the production is: 20 Lf/ml for the monolysigens, 30 Lf/ml for the tandem twinlysigens and 60 Lf/ml for the nontandem twinlysigens.

EXAMPLE 2

By the same procedure as set forth in Example 1, there are prepared the inocula of $C_7$ ($\beta$45)$M_3$, $C_7$ ($\beta$45) $M_{11}$ and $C_7$ ($\beta$45) $M_8$.

0.1 ml of each culture is inoculated in 125-ml flasks, each containing 10 mls of deferritized CY medium and supplemented with 0.1 μg/ml of $Fe^{++}$.

The flasks are placed to incubate for 36 hours at a temperature of 35° C. on a rotary stirrer (240 RPM). Samples taken after 20 hours and 30 hours as from the start of the fermentation are analysed with the same procedure as reported in Example 1 for determining the optical density and the production of the CRM 45 released in the supernatant.

The results which have been obtained are tabulated below:

TABLE 1

| Lysogenic strains | Optical 20 hrs | Density 30 hrs | CRM 45 20 hrs | μg/ml 30 hrs |
|---|---|---|---|---|
| $C_7$($\beta$45)$M_3$ | 4.5 | 9.7 | 16 | 31.5 |
| $C_7$($\beta$45)$M_{11}$ | 4.5 | 9.8 | 22 | 42 |

TABLE 1-continued

| Lysogenic strains | Optical Density 20 hrs | 30 hrs | CRM 45 20 hrs | µg/ml 30 hrs |
|---|---|---|---|---|
| $C_7(\beta 45)M_8$ | 4.7 | 10 | 40 | 70 |

The results reported above show that the maximum production of CRM 45 is detected after 30 hours of culturing and is virtually the same for the monolysigens and the tandem twinlysigens and is nearly twice as much for the nontandem lysigens.

EXAMPLE 3

A preculture of the lysigen $G_7$ ($\beta 45$)$M_8$ was prepared such as described in Example 1, and 2 mls of such preculture have been transferred into two 2.000-ml Erlenmeyer flasks, each containing 500 mls of deferritized CY medium and supplemented with 0.1 µg/ml of $Fe^{++}$ and cultured with stirring (240 RPM) at a temperature of 35° C. for 24 hours.

1.000 mls of the resultant lysigen culture were inoculated in 40 liters of a CY culturing medium having a concentration of $Fe^{++}$ ions of 0.1 µg/ml, contained in a pot fermentor having a volume of 50 liters and cultured at a temperature of 37° C. by aerating at a rate of 15 l/min from bottom to top, stirring at 600 RPM and maintaining the pH of the culturing medium from 6.5 to 7.5 with a 20%-glucose solution, or with 4-normal NaOH for a period of 40 hours. The quantiy of CRM 45 after 30 hours of fermentation was 200 Lf/ml. The resultant broth culture was centrifuged in a continuous-flow centrifuge and the protein was recovered from the supernatant by precipitating it with ammonium sulphate supplemented to a degree of saturation of 75%.

The slurry thus obtained was centrifuged and the sediment, upon washing with pH 7.5 phosphate buffer was purified through a column charged with an ion-exchange resin (Dimethylammoniumethylcellulose).

The protein was recovered by eluting the column with a sodium chloride gradient, with a yield of 80%.

I claim:

1. A process for the production of protein cross reacting with diptheria toxin comprising the step of culturing in a liquid nutrient medium with a concentration of iron ions of from 0.05 µg/ml to 0.5 µg/ml and at a temperature of from 30° C. to 40° C. at a neutral pH and under aerobic conditions, a microorganism belonging to Corynebacterium diphtheriae with two mutant phages encoding for the protein cross reacting with diphtheria toxin and integrated nontandemly at attachment sites $B_1$ and $B_2$ of the bacterial chromosome wherein the protein is CRM 197 protein and the microorganism is the $C_7(197)$ M, ATCC-39255 strain with two 197 mutant phages integrated nontandemly in said attachments sites $B_1$ and $B_2$.

2. A process according to claim 1, characterized in that the concentration of iron ions in the liquid nitrient medium is 0.1 µg/ml.

3. A process for the production of protein cross reacting with diptheria toxin comprising the step of culturing in a liquid nutrient medium with a concentration of iron ions of from 0.05 µg/ml to 0.5 µg/ml and at a temperature of from 30° C. to 40° at a neutral pH and under aerobic conditions, a microorganism belonging to Corynebacterium diphtheriae with two mutant phages encoding for the protein cross reacting diphteria toxin and integrated nontandemly at attachment sites $B_1$ and $B_2$ of the bacterial chromosome wherein the protein is CRM45 protein and the microorganism is the $C_7(45)$ $M_8$ ATCC 39526 strain with two mutant 45 phages integrated nontandemly in said attachment sites $B_1$ and $B_2$.

* * * * *